United States Patent [19]

Hagen et al.

[11] Patent Number: 5,670,704
[45] Date of Patent: Sep. 23, 1997

[54] SELECTIVE PRODUCTION OF 2,6-DIMETHYLNAPHTHALENE

[75] Inventors: Gary P. Hagen, West Chicago, Ill.; Deborah T. Hung, Cambridge, Mass.

[73] Assignee: Amoco Corporation, Chicago, Ill.

[21] Appl. No.: 544,275

[22] Filed: Jun. 26, 1990

[51] Int. Cl.$^6$ .................................................. C07C 15/12
[52] U.S. Cl. .......................... 585/471; 585/472; 585/474
[58] Field of Search ................................ 585/471, 472, 585/474

[56] References Cited

U.S. PATENT DOCUMENTS

| | | | |
|---|---|---|---|
| 2,388,758 | 11/1945 | Mills, Jr. | 585/474 |
| 4,454,364 | 6/1984 | Farcasiu et al. | 585/472 |
| 4,873,386 | 10/1989 | Hagen et al. | 585/472 |
| 4,950,824 | 8/1990 | Shiroto et al. | 585/474 |

FOREIGN PATENT DOCUMENTS

| | | |
|---|---|---|
| 61-831137 | 4/1986 | Japan . |
| 62-252733 | 11/1987 | Japan . |

OTHER PUBLICATIONS

Olah et al., "Alkylation of Naphthalene with Alkyl Halides"; J. Am. Chem. Soc., 98:7, pp. 1839–1842; Mar. 1976.

Shimada et al; "Ethylation and Transethylation of Naphthalene"; Bulletin of the Chem. Soc. of Japan; vol. 48(II); pp. 3306–3308; Nov., 1975.

*Primary Examiner*—Glenn A. Caldarola
*Assistant Examiner*—E. D. Irzinski
*Attorney, Agent, or Firm*—Thomas E. Nemo; Wallace L. Oliver

[57] ABSTRACT

A method for the highly selective production of 2,6-dimethlynaphthalene by the transmethylation of naphthalene or 2-methylnaphthalene by the use of a specific acid catalyst and a highly regeospecific methylating agent.

15 Claims, No Drawings

SELECTIVE PRODUCTION OF 2,6-DIMETHYLNAPHTHALENE

BACKGROUND OF THE INVENTION

1. Field of the Invention

This invention relates to the production of a dimethylnaphthalene and more particularly concerns the highly selective production of 2,6-dimethylnaphthalene by the transmethylation of naphthalene or 2-methylnaphthalene by 1,2,4,5-tetramethylbenzene, pentamethylbenzene or hexamethylbenzene.

2. Description of the Prior Art 2,6-Naphthalene dicarboxylic acid is a monomer that is known to be useful for the preparation of a variety of polymers. For example, poly(ethylene 2,6-naphthalate) which has better heat resistance and mechanical properties than polyethylene terephthalate and is useful in the manufacture of films and fibers, is prepared from 2,6-naphthalene dicarboxylic acid and ethylene glycol.

2,6-Dimethylnaphthalene is a desirable feedstock for oxidation to 2,6-naphthalene dicarboxylic acid. A known conventional process for producing 2,6-naphthalene dicarboxylic acid comprises the oxidation of 2,6-dimethylnaphthalene with oxygen in the liquid phase in an acetic acid solvent at an elevated temperature and pressure and in the presence of a catalyst comprising cobalt, manganese and bromine components.

Dimethylnaphthalenes can be found in low concentrations in refinery streams as mixtures of some or all of the ten possible dimethylnaphthalene isomers, including 2,6-dimethylnaphthalene. However, separation of these isomers is very difficult and expensive. Consequently, methods for producing specific dimethylnaphthalenes or mixtures of two or three specific dimethylnaphthalenes in high purity and quality are highly desirable. Olah et al., "Alkylation of Naphthalene with Alkyl Halides," Journal of American Chemical Society, 98:7, pages 1839–1842 (Mar. 31, 1976), disclose that theretofor there was no clear understanding of directive effects and selectivities for the Friedel-Crafts alkylation of naphthalene.

Since then, Japanese Kokai Patent Application Publication No. 61-83137 (Apr. 26, 1986) discloses a synthesis involving the transalkylation of naphthalene or a 2-methylnaphthalene in the presence of an aluminum chloride catalyst at 0°–35° C. in the liquid phase to produce a 2,6-dialkylnaphthalene. Suitable alkylating agents are disclosed as including durene, diethylbenzene, triethylbenzene, triisopropylbenzene, isopropylxylene, and dibutylbenzene. The reported results indicate a relatively low degree of selectivity for the formation of specific dialkylnaphthalenes. Furthermore, it is specifically stated that the disclosed alkylation method must be performed at 0°–35° C., preferably room temperature, and that the higher the reaction temperature, the lower the selectivity for the formation of beta-alkyl substituted naphthalene and especially 2,6-dialkylnaphthalene. In addition although this published patent application specifically mentions durene (1,2,4,5-tetramethylbenzene) as an example of an alkylation agent, it contains actual examples that illustrate only the use as alkylating agents in the method disclosed therein of polyalkylbenzenes where the alkyl groups are larger than methyl groups, and indicates as follows that polyalkylbenzenes with alkyl groups other than methyl groups afford benefits in the method disclosed therein: "Polyalkylbenzenes with ethyl, propyl, or butyl groups with high-carbon alkyl groups have high reaction rates . . . " Moreover, this published Japanese patent application states that, when the naphthalene is solid at reaction temperature disclosed therein, a solvent such as a paraffin or cycloparaffin should be employed. This published patent application also discusses the use of halogenated alkyls in the alkylation of naphthalenes as a prior art method which did not produce a beta-alkyl naphthalene with the desired selectivity.

Japanese Kokai Patent Application Publication No. 62-252733 (Nov. 4, 1987) discloses a process for the transethylation of biphenyl with an ethylbenzene to form monoethylbiphenyl and diethylbiphenyl in the presence of a Friedel-Crafts catalyst, such as aluminum chloride, at 70°–150° C. This published Japanese patent application discloses that a reaction temperature of less than 70° C. delays the reaction rate. The ring positions of the ethyl substituents in the ethylated biphenyl products are not disclosed. Suitable ethylbenzenes are disclosed as including ethylbenzene, diethylbenzene, triethylbenzene, tetraethylbenzene, other ethyl-substituted benzenes, ethyltoluene, diethyltoluene and other ethyl-substituted toluenes. Polyethylbenzenes containing relatively small amounts of monoethylbenzene, triethylbenzene and tetraethylbenzene can also be used advantageously.

Shimada et al., "Ethylation and Transethylation of Naphthalene," Bulletin of the Chemical Society of Japan, Vol. 48 (11), pages 3306–3308 (November, 1975) disclose the transethylation of naphthalene by ethylbenzene or ethylxylenes to form monoethylnaphthalenes in the presence of an aluminum chloride catalyst at 20°–30° C. The rates of transethylation with ethylxylene isomers were reported to decrease in the order of 1,2-dimethyl-4-ethylbenzene$\geq$, 1,3-dimethyl-4-ethylbenzene$\geq$, 1,4-dimethyl-2-ethylbenzene$\geq$1,3-dimethyl-5-ethylbenzene.

Japanese Patent Application 35/391/48, published on Oct. 18, 1989, discloses a method for the preparation of ethyldiphenylethane or diethyldiphenylethane by the transethylation of diphenylethane with polyethylbenzene(s) in the presence of a Friedel-Crafts catalyst at 0°–150° C. Preferred catalysts are aluminum chloride, aluminum bromide and boron trifluoride. Transethylation of 1,1-diphenylethane by this method produces either 1-phenyl-1-ethylphenylethane, 1-phenyl-1-diethylphenylethane or 1,1-bis(ethylphenyl) ethane. The ring positions of the ethyl substituents in the ethylated products are not disclosed.

Thus, until recently, no existing method was known for the highly selective production of 2,6-dialkylnaphthalene or of a mixture of 2,6- and 2,7-dialkylnaphthalenes by a transalkylation process. Then Hagen et al., U.S. Pat. No. 4,873,386, issued on Oct. 10, 1989, disclosed a method for producing 2,6-diethylnaphthalene, which comprises: reacting in the liquid phase at least one of naphthalene or 2-ethylnaphthalene as the feed with at least one of 1,4-diethylbenzene, 1,2,4-triethylbenzene, at least one tetraethylbenzene or pentaethylbenzene as the ethylating agent per mole of the feed by weight, in the presence of a Lewis acid catalyst selected from the group consisting of aluminum chloride, aluminum bromide, tantalum chloride, antimony fluoride, and red oil, at a level of from about 0.01 to about 1 mole of the catalyst per mole of the feed (for red oil, based on the content of aluminum chloride content of the red oil) by weight and at a temperature in the range of from about $-10°$ C. to about $100°$ C. In particular, Hagen et al., disclose that 1,2,3,4- and 1,2,3,5-tetraethylbenzenes, as well as 1,2,4,5-tetraethylbenzene, are useful ethylating agents, but that hexaethylbenzene is not. Hagen et al. further disclose that 2,6-diethylnaphthalene is formed at a higher selectivity and yield when 2-ethylnaphthalene is transethylated and that pentaethylbenzene and any tetraethylbenzene are the preferred ethylating agents.

However, because of the relative unavailability of 2-ethylnaphthalene for use as the preferred feedstock for the aforesaid method of Hagen et al. and because of the benefit in efficiency in oxidizing the dialkylnaphthalene of the lowest possible molecular weight—that is, dimethylnaphthalene—to 2,6-naphthalene dicarboxylic acid, it is highly desirable to devise a method for the Friedel-Crafts transmethylation of naphthalene or 2-methylnaphthalene to 2,6-dimethylnaphthalene. However, the aforesaid Olah et al. paper disclose poor selectivities and/or low conversions for the direct methylation of naphthalene or 2-methylnaphthalene using a simple methlyating agent such as methyl halides or methanol to provide beta-substituted products such as 2,6-dimethylnaphthalenes.

OBJECTS OF THE INVENTION

It is therefore a general object of the present invention to provide an improved method for the highly selective production of 2,6-dimethylnaphthalene or a mixture of 2,6- and 2,7-dimethylnaphthalenes.

More specifically, it is an object of the present invention to provide an improved method for the highly selective production of 2,6-dimethylnaphthalene or a mixture of 2,6- and 2,7-dimethylnaphthalenes by transmethylating naphthalene or 2-methylnaphthalene under highly regeospecific conditions.

Other objects and advantages of the invention will become apparent upon reading the following detailed description and appended claims.

SUMMARY OF THE INVENTION

These objects are achieved by an improved method for producing 2,6-dimethylnaphthalene, comprising: reacting at least one of naphthalene of 2-methylnaphthalene as the feed in the liquid phase with a methylating agent selected from the group consisting of at least one of 1,2,4,5-tetramethylbenzene, pentamethylbenzene or hexamethylbenzene at a level of from about 1 to about 10 moles of the methylating agent per mole of the feed, in the presence of a Lewis acid or a Bronsted acid alkylation catalyst or mixture thereof that is more acidic than ferric chloride and at least as acidic as ferric bromide, at a level of from about 0.01 to about 1 mole of the catalyst per mole of the feed and at a temperature in the range of from about −40° to about 80° C.

DETAILED DESCRIPTION OF THE PREFERRED EMBODIMENTS

Naphthalene or 2-methylnaphthalene or a mixture thereof is the feed in the method of this invention. Preferably the feed comprises 2-methylnaphthalene. The feed must be either dissolved in a suitable solvent as described hereinbelow or must be a liquid at the reaction temperature employed.

As illustrated in the examples hereinbelow, relative to the dimethylbenzenes, trimethylbenzenes, and 1,2,3,4- and 1,2,3,5-tetramethylbenzenes, the following are the only suitable methylating agents in the method of this invention: 1,2,4,5-tetramethylbenzene (durene), pentamethylbenzene and hexamethylbenzene. The mole ratio of the methylating agent-to-naphthalene and/or 2-methylnaphthalene feed is in the range of from about 1:1, preferably from about 2:1, to about 10:1, preferably to about 5:1, in the method of this invention.

The transmethylation reaction of the present invention is conducted in the liquid phase in the presence or absence of a solvent. Any liquid that is inert under the reaction conditions employed and serves as an effective solvent for the reactants and products is suitable for use as a solvent in the method of this invention. Suitable solvents include halocarbons, such as methylene chloride, chlorobenzene, 1,1-dichloroethane, 1,2-dichloroethane, and chloroform, or carbon disulfide, benzene, cyclohexane, and n-octane. Solvents which are basic and bind irreversibly with the catalyst are not suitable. Such unsuitable solvents include ketones, aldehydes, ethers, esters and alcohols. Preferably the solvent is methylene chloride. If a solvent is employed, the weight ratio of solvent-to-feed compound is in the range of from about 1:1, preferable from about 2:1, to about 15:1, preferably to about 8:1.

Lewis acids and Bronsted acids or mixtures thereof that are conventionally used as alkylation catalysts and that are more acidic than ferric chloride and at least as acidic as ferric bromide, and preferably at least as acidic as aluminum chloride and that do not decompose under the conditions employed in the method of this invention, are suitable for use as the catalyst in the method of this invention. Suitable Lewis acid catalysts include aluminum chloride, aluminum bromide, tantalum pentachloride, antimony pentafluoride, boron trichloride, ferric bromide, sulfonated zirconia, trifluoromethanesulfonic acid and "red oil," which is a complex polar liquid catalyst phase which is synthesized by addition of ethyl chloride or bromide or hydrogen chloride or bromide to a slurry of aluminum chloride or some other aforesaid suitable Lewis Acid in an aromatic solvent such as benzene, methylbenzene, or mixed dimethylbenzenes or mixed tetramethylbenzenes and which forms a separate liquid phase below the phase containing the feed. Preferably, aluminum chloride or red oil containing aluminum chloride is the catalyst.

The catalyst can be employed as a separate immiscible layer such as the aforementioned red oil, or it can be dissolved with the reactants and product in an organic solvent such as methylene chloride or chlorobenzene. Thus, depending upon the selection of solvent for the catalyst, the feed, methylating agent and catalyst can be present in a single liquid phase, or the feed and catalyst can be present in separate liquid phases. In the alternative, the catalyst can be in the form of a solid, for example, aluminum chloride deposited on graphite or aluminum chloride intercalated with graphite. The catalyst is employed in the method of this invention at a level in the range of from about 0.01, preferably from about 0.05, to about 1.0, preferably to about 0.2 mole per mole of the total of naphthalene and 2-methylnaphthalene employed. In general, the greater the amount of catalyst employed relative to the amount of feed employed, the greater are the rate of the transmethylation reaction and the extent of conversion of the feed.

Other conventional Lewis acids such as antimony chloride, bismuth chloride, ferric chloride, tin chloride, titanium chloride, and zinc chloride are not such effective catalysts in the method of the present invention.

If the reaction is performed continuously or batchwise, the residence time is from about 0.1, preferably from about 1, to about 10, preferably to about 5 hours. The reaction temperature is in the range of from about −40° C., preferably from about 0° C., to about 80° C., preferably to about 60° C. The reaction pressure must be sufficiently high to maintain the reactants and products in the liquid phase at the particular reaction temperature employed, and generally is in the range of from about 0.5, preferably from about 0.8, to about 10, preferably to about 5, atmospheres gauge.

Preferably, when a polar solvent is not employed, a hydrogen halide, such as hydrogen chloride, or an alkyl, alkylene, or alkylidene halide is employed as a promoter in the method of the present invention. Typically, such alkyl, alkylene or alkylidene halides include a methyl halide, such as methyl chloride, or a methylene, ethylene or ethylidene halide. The promoter is employed at a level of from about 0.1, preferably from about 0.5, up to about 100, preferably up to at least 2 moles per mole of catalyst (for red oil, based on the aluminum chloride content of the red oil). When the solvent is an alkyl or alkylene halide, it also serves as a promoter in the method of this invention.

The present invention will be more clearly understood from the following specific examples.

EXAMPLES 1–23

Except as indicated hereinbelow, each of Examples 1–23 was performed using a 250 milliliter, 3-neck round bottom flask equipped with a magnetic stirrer, purged with nitrogen and cooled in an ice bath. 2-Methylnaphthalene (2-MN) was the feed in Examples 1–20, and naphthalene (NP) was the feed in Examples 21–23. The components of the reaction mixture that are identified in Table 1 were introduced in the amounts and under the reaction conditions specified in Table 1. In each case, the catalyst was introduced last, at which point the transmethylation reaction commenced immediately. Generally, twenty-four hours after the catalyst was introduced, methanol in a volume that was approximately twice the volume of the reaction medium, was introduced to quench the reaction. The product mixture was then analyzed to determine the weight percent of 2-methylnaphthalene or naphthalene that is converted ("Conversion"), the "Yield" or the mole percent of 2-methylnaphthalene or naphthalene that is converted selectively to 2,6- and 2,7-dimethylnaphthalenes (identified as 2,6-DMN and 2,7-DMN, respectively, in Table 2), and the "Selectivity" or relative mole percent of each of 2,6-dimethylnaphthalene and 2,7-dimethylnaphthalene in the combined amounts of products produced in each example. The Yield is also the quotient obtained by dividing 100 into the product of the Conversion multiplied by the Selectivity.

In Table 1, HMB means hexamethylbenzene; PMB means pentamethylbenzene; 1,2,4,5-TeMB means 1,2,4,5-tetramethylbenzene (durene); 1,2,3,4-TeMB means 1,2,3,4-tetramethylbenzene; 1,2,3,5-TeMB means 1,2,3,5-tetramethylbenzene; and 1,2,4-TMB means 1,2,4-trimethylbenzene.

Comparison of the results in Table 2 for Examples 3, 4 and 5 illustrates that methylation reactivity and the provision of yields of desired methylation products vary in descending order depending on whether 1,2,4,5-tetramethylbenzene, pentamethylbenzene or hexamethylbenzene is employed as the methylating agent. In Examples 3, 4 and 5, two phases are present, with the reactants and products dissolved in cyclohexane, and aluminum chloride dissolved in a separate red oil catalyst liquid phase. Comparison of the results of Examples 6, 9 and 10 illustrates the same variation and dependence, but in a reaction system in which all of the reactants, products and aluminum chloride catalyst are dissolved in a single phase in a methylene chloride solvent. Comparison of the results of Examples 6, 7 and 8 illustrates that methylation reactivity and provision of the desired methylation products vary in descending order depending on whether 1,2,4,5-tetramethylbenzene, 1,2,3,4-tetramethylbenzene or 1,2,3,5-tetramethylbenzene is employed as the methylating agent.

Comparison of the results of Examples 11 and 15 illustrates that the use of relatively greater amounts of the catalyst affords higher reaction rates and

TABLE 1

| Example No. | Methylating Agent Compound | Amount[1] | Catalyst Compound | Amount[1] | Reaction Temperature (°C.) | Solvent Compound | Amount[4] | Promoter Compound | Amount |
|---|---|---|---|---|---|---|---|---|---|
| 1 | HMB | 1.0 | $AlCl_3$[5] | 0.4 | 40 | $C_6H_{12}$[3] | 50/.0697 | None | — |
| 2 | HMB | 1.0 | $AlCl_3$[7] | 0.4 | 20–50 | $C_6H_{12}$[3] | 30/.0697 | HCl | Sat'd. |
| 3 | 1,2,4,5-TeMB | 1.0 | $AlCl_3$[7] | 0.4 | 40 | $C_6H_{12}$[3] | 30/.0745 | HCl | Sat'd |
| 4 | PMB | 1.0 | $AlCl_3$ | 0.4 | 20–50 | None | — | None | — |
| 5 | HMB | 1.0 | $AlCl_3$[7] | 0.4 | 40 | $C_6H_{12}$[3] | 30/.0616 | HCl | Sat'd |
| 6 | 1,2,4,5-TeMB | 2.0 | $AlCl_3$ | 0.4 | 20 | $CH_2Cl_2$ | 20/.0127 | Solvent | 20/.0127[4] |
| 7 | 1,2,3,4-TeMB | 2.0 | $AlCl_3$ | 0.4 | 20 | $CH_2Cl_2$ | 20/.0127 | Solvent | 20/.0127[4] |
| 8 | 1,2,3,5-TeMB | 2.0 | $AlCl_3$ | 0.4 | 20 | $CH_2Cl_2$[2] | 20/.0127 | Solvent | 20/.0127[4] |
| 9 | PMB | 2.0 | $AlCl_3$ | 0.4 | 20 | $CH_2Cl_2$[2] | 20/.0127 | Solvent | 20/.0127[4] |
| 10 | HMB | 2.0 | $AlCl_3$ | 0.4 | 20 | $CH_2Cl_2$[2] | 20/.0127 | Solvent | 20/.0127[4] |
| 11 | HMB/1,2,4-TMB | 1.0/1.0 | $AlCl_3$ | 0.4 | 40 | $C_6H_{12}$[3] | 20/.057 | HCl | Sat'd. |
| 12 | HMB/1,2,4-TMB | 0.5/0.5 | $AlCl_3$ | 0.4 | 40 | $C_6H_{12}$[3] | 20/.057 | HCl | Sat'd. |
| 13 | HMB | 1.0 | $AlCl_3$[5] | 0.4 | 50 | $C_6H_{12}$[3] | 75/.0697 | None | — |
| 14 | HMB | 1.0 | $SbF_5$[6] | 0.4 | 0–50 | $C_6H_{12}$[3] | 30/.0697 | None | — |
| 15 | HMB/1,2,4-TMB | 1.0/1.0 | $AlCl_3$ | 1.0 | 40 | $C_6H_{12}$[3] | 30/.0582 | HCl | Sat'd |
| 16 | HMB | 1.0 | $AlCl_3$[7] | 0.4 | 20 | $C_6H_{12}$[3] | 50/.0697 | HCl | Sat'd |
| 17 | 1,2,4,5-TeMB | 2.0 | $AlCl_3$ | 0.4 | 20 | $CH_2Cl_2$[2] | 10/.0127 | Solvent | 10/.0127[4] |
| 18 | 1,2,4,5-TeMB | 2.0 | $AlCl_3$ | 0.4 | 20 | $C_6H_5Cl$[2] | 20/.0127 | Solvent | 20/.0127[4] |
| 19 | 1,2,4,5-TeMB | 2.0 | $AlCl_3$ | 1.0 | 0 | $CH_2Cl_2$[2] | 30/.025 | Solvent | 30/.025[4] |
| 20 | 1,2,4,5-TeMB | 2.0 | $AlCl_3$ | 1.0 | 0 | $CH_2Cl_2$[2] | 30/.025 | Solvent/$CH_3I$ | 30/.025[4]-1[1] |
| 21 | 1,2,4,5-TeMB | 4.0 | $AlCl_3$ | 1.0 | 0 | $CH_2Cl_2$[2] | 30/.0025 | Solvent | .30/.0025[4] |
| 22 | 1,2,4,5-TeMB | 4.0 | $AlCl_3$ | 1.0 | 0 | $CH_2Cl_2$[2] | 30/.0025 | Solvent/$CH_3I$ | 30/.0025[4]-1[1] |
| 23 | 1,2,4,5-TeMB | 4.0 | $AlCl_3$ | 1.0 | 20 | $CH_2Cl_2$[2] | 30/.0025 | Solvent | 30/.0025[4] |

Footnotes
[1]moles per mole of 2-MN or NP
[2]dissolves reactants, product and catalyst
[3]dissolves reactants and product, but not catalyst
[4]milliliters of solvent per moles of 2-MN or NP employed
[5]intercalated on graphite, $AlCl_3$ being 35 weight percent of the composite
[6]intercalated on graphite, $SbF_5$ being 50 weight percent of the composite
[7]red oil catalyst, with a separate liquid phase formed of $AlCl_3$ when HCl is passed through the $C_6H_{12}$ phase

TABLE 2

| Example No. | Reaction Time[1] | Conversion[2] | Yield[3] 2,6-DMN | Yield[3] 2,7-DMN | Selectivity[4] 2,6-DMN | Selectivity[4] 2,7-DMN |
|---|---|---|---|---|---|---|
| 1 | 150 | 0.33 | 0.33 | 0 | 100 | 0 |
|   | 180 | 0.74 | 0.63 | 0.12 | 84.3 | 15.7 |
|   | 210 | 1.1 | 0.89 | 0.19 | 82.2 | 17.8 |
| 2 | 60 | 0 | — | — | — | — |
|   | 150 | 0 | — | — | — | — |
|   | 210 | 0.326 | 0.326 | 0 | 100 | 0 |
|   | 270 | 3.10 | 2.40 | 0.70 | 77.46 | 22.54 |
|   | 345 | 15.98 | 10.00 | 3.92 | 62.59 | 24.50 |
|   | 390 | 47.71 | 20.93 | 7.08 | 43.87 | 14.84 |
|   | 435 | 71.12 | 24.11 | 8.33 | 33.90 | 11.71 |
|   | 495 | 83.98 | 22.15 | 7.61 | 26.37 | 9.06 |
| 3 | 30 | 7.16 | 5.96 | 0.83 | 83.21 | 11.62 |
|   | 60 | 33.60 | 20.93 | 7.77 | 62.31 | 23.14 |
|   | 120 | 44.47 | 23.23 | 9.32 | 52.24 | 20.96 |
| 4 | 210 | 0 | 0 | 0 | 0 | 0 |
|   | 390 | 1.632 | 1.22 | 0.42 | 74.56 | 25.44 |
|   | 510 | 9.50 | 6.20 | 2.68 | 65.20 | 28.21 |
| 5 | 30 | 0.98 | 0.76 | 0.22 | 77.78 | 22.22 |
|   | 60 | 1.73 | 1.33 | 0.41 | 76.41 | 23.59 |
|   | 120 | 7.34 | 5.07 | 2.17 | 69.03 | 29.48 |
|   | 420 | 71.78 | 28.74 | 10.68 | 40.04 | 14.89 |
|   | 540 | 82.88 | 25.22 | 9.40 | 30.43 | 11.34 |
| 6 | 30 | 10.2 | 7.73 | 2.50 | 75.4 | 24.5 |
|   | 90 | 35.6 | 22.3 | 8.9 | 62.7 | 25.0 |
|   | 120 | 41.5 | 25.3 | 10.34 | 61.0 | 25.0 |
| 7 | 30 | 3.8 | 3.0 | 0.78 | 79.6 | 20.4 |
|   | 60 | 7.4 | 5.6 | 1.78 | 76.0 | 24.0 |
|   | 120 | 11.6 | 8.6 | 2.82 | 73.7 | 24.3 |
| 8 | 30 | 0.27 | 0.27 | 0 | 100 | 0 |
|   | 60 | 0.69 | 0.69 | 0 | 100 | 0 |
|   | 120 | 2.1 | 1.6 | 0.52 | 75.3 | 24.7 |
| 9 | 30 | 1.3 | 1.1 | 0.27 | 78.9 | 21.1 |
|   | 60 | 3.0 | 2.3 | 0.72 | 75.9 | 24.1 |
|   | 120 | 7.3 | 5.1 | 2.15 | 70.5 | 29.5 |
| 10 | 30 | 0 | 0 | 0 | 0 | 0 |
|   | 60 | 0 | 0 | 0 | 0 | 0 |
|   | 120 | 0 | 0 | 0 | 0 | 0 |
| 11 | 120 | 0.55 | 0.55 | 0 | 100 | 0 |
|   | 180 | 1.80 | 1.40 | 0.40 | 77.67 | 22.31 |
|   | 240 | 2.95 | 2.11 | 0.84 | 71.37 | 28.63 |
|   | 420 | 9.65 | 6.16 | 2.67 | 63.84 | 27.68 |
|   | 530 | 29.27 | 18.07 | 7.13 | 61.73 | 24.35 |
|   | 750 | 55.36 | 28.67 | 10.44 | 51.79 | 18.86 |
|   | 870 | 68.63 | 30.58 | 11.06 | 44.42 | 16.06 |
| 12 | 60 | 0.33 | 0.33 | 0 | 100 | 0 |
|   | 120 | 1.50 | 1.17 | 0.33 | 78.05 | 21.95 |
|   | 210 | 14.15 | 9.1 | 3.68 | 64.88 | 26.01 |
|   | 240 | 16.55 | 10.92 | 4.25 | 65.69 | 26.51 |
|   | 360 | 30.65 | 19.77 | 7.01 | 64.50 | 22.85 |
|   | 480 | 46.25 | 27.27 | 9.81 | 58.97 | 21.22 |
|   | 660 | 64.78 | 27.78 | 10.28 | 42.86 | 15.87 |
| 13 | 90 | 0.49 | 0.017 | 0 | 100 | 0 |
|   | 120 | 1.14 | 0.95 | 0.19 | 83.07 | 16.93 |
|   | 180 | 2.67 | 2.12 | 0.54 | 79.78 | 20.22 |
| 14 | 90 | 0 | 0 | 0 | 0 | 0 |
|   | 120 | 0.232 | 0.232 | 0 | 100 | 0 |
|   | 180 | 0.489 | 0.489 | 0 | 100 | 0 |
| 15 | 90 | 3.22 | 2.33 | 0.89 | 72.38 | 27.62 |
|   | 120 | 6.40 | 4.32 | 1.74 | 67.48 | 27.19 |
|   | 180 | 15.50 | 10.34 | 4.30 | 66.73 | 27.74 |
| 16 | 990 | 3.5 | 2.58 | 0.72 | 74.4 | 20.6 |
|   | 1440 | 8.1 | 5.64 | 2.07 | 69.6 | 25.5 |
|   | 2430 | 26.70 | 17.90 | 5.92 | 67.04 | 22.16 |
|   | 2670 | 34.29 | 20.19 | 7.28 | 58.88 | 21.23 |
|   | 2910 | 40.96 | 22.80 | 7.31 | 55.86 | 17.85 |
|   | 3180 | 66.05 | 26.43 | 8.48 | 40.02 | 12.84 |
| 17 | 30 | 28.8 | 17.1 | 6.7 | 59.3 | 23.4 |
|   | 60 | 50.5 | 25.9 | 10.6 | 51.2 | 21.0 |
|   | 120 | 66.2 | 27.4 | 11.9 | 41.3 | 18.0 |
| 18 | 30 | 0 | — | — | 0 | 0 |
|   | 60 | 1.96 | 1.47 | 0.49 | 75.0 | 25.0 |
|   | 120 | 8.10 | 5.19 | 2.37 | 64.1 | 29.3 |
| 19 | 30 | 1.4 | 1.4 | 0 | 100.0 | 0 |
|   | 60 | 6.5 | 4.7 | 1.8 | 71.8 | 28.2 |
|   | 120 | 28.5 | 20.1 | 7.0 | 70.5 | 24.4 |
| 20 | 30 | 0.7 | 0.7 | 0 | 100.0 | 0 |
|   | 60 | 14.4 | 5.9 | 2.4 | 41.2 | 16.3 |
|   | 180 | 48.4 | 28.6 | 10.2 | 59.0 | 21.1 |
| 21 | 120 | 3.8 | 3.8 | 0 | 100 | 0 |
|   | 180 | 11.4 | 8.4 | 3.1 | 73.2 | 26.8 |
|   | 420 | 76.9 | 15.5 | 8.2 | 20.1 | 10.7 |
| 22 | 90 | 8.6 | 6.3 | 2.4 | 72.7 | 27.2 |
|   | 180 | 20.7 | 14.7 | 5.5 | 72.6 | 27.4 |
|   | 360 | 69.9 | 18.0 | 8.8 | 25.7 | 12.6 |
| 23 | 30 | 34.3 | 24.8 | 9.5 | 72.2 | 27.8 |
|   | 60 | 73.2 | 24.2 | 12.8 | 33.0 | 17.4 |
|   | 120 | 88.3 | 11.4 | 6.2 | 12.9 | 6.9 |

Footnotes
[1] minutes
[2] mole percent of 2-MN or NP converted
[3] mole percent of 2-MN or NP converted to 2,6-DMN or 2,7-DMN
[4] mole percent of 2,6-DMN or 2,7-DMN in products yields. Comparison of the results of Examples 1 and 14 illustrates that the use of aluminum chloride intercalated on graphite is substantially more effective as a solid catalyst in the method of this invention than is antimony pentafluoride intercalated on graphite.

Comparison of the results of Examples 1, 2, 5, 11 and 16 illustrates that the use of higher reaction temperatures affords higher rates of the methylation reaction but that the highest yields of desired products are obtained at a reaction temperature of 40° C.

Comparison of the results of Examples 6, 17 and 18 illustrates that the methylation reaction proceeds more rapidly and with a greater degree of conversion of 2-methylnaphthalene when a haloaliphatic solvent is employed rather than a haloaromatic solvent and when relatively low levels rather than higher levels, of the haloaliphatic solvent are employed.

The results of Examples 21–23 illustrate that naphthalene is also effectively transmethylated to 2,6-dimethylnaphthalene.

From the above description, it is apparent that the objects of the present invention have been achieved. While only certain embodiments have been set forth, alternative embodiments and various modifications will be apparent from the above description to those skilled in the art. These and other alternatives are considered equivalents and are within the spirit and scope of the present invention.

Having described the invention, what is claimed is:

1. A method for producing 2,6-dimethylnaphthalene, comprising: reacting at least one of naphthalene or 2-methylnaphthalene as the feed in the liquid phase with a methylating agent selected from the group consisting of at least one, pentamethylbenzene or hexamethylbenzene at a level of from about 1 to about 10 moles of the methylating agent per mole of the feed, in the presence of a catalyst comprising a Lewis acid or Bronsted acid alkylation catalyst or mixture thereof that is more acidic than ferric chloride and at least as acidic as ferric bromide, at a level of from about 0.01 to about 1 mole of the catalyst (for red oil, based on the aluminum chloride content of the red oil) per mole of the feed and at a temperature in the range of from about −40° C. to about 80° C.

2. The method of claim 1 wherein the feed comprises 2-methylnaphthalene.

3. The method of claim 1 wherein the methylating agent is hexamethlbenzene.

4. The method of claim 1 wherein the methylating agent is at a level of from about 2 to about 5 moles per mole of the feed.

5. The method of claim 1 wherein the catalyst comprises aluminum chloride, aluminum bromide, boron trichloride, tantalum pentachloride, antimony pentafluoride ferric bromide, sulfonated zirconia, trifluoromethanesulfonic acid or red oil.

6. The method of claim 1 wherein the catalyst comprises red oil or aluminum chloride.

7. The method of claim 1 wherein the catalyst is at a level of from 0.05 to about 0.2 mole per mole of the feed.

8. The method of claim 1 wherein the reaction is conducted at a temperature in the range of from about 0° C. to about 60° C.

9. The method of claim 1 wherein the reaction is conducted in the presence of a promoter comprising a hydrogen halide or an alkyl, alkylene or alkylidene halide, at a level of from about 0.1 to about 100 moles per mole of the catalyst.

10. The method of claim 9 wherein the promoter is hydrogen chloride or methylene chloride.

11. The method of claim 1 wherein the feed and methylating agent are dissolved in a solvent.

12. The method of claim 1 wherein the catalyst is dissolved in a solvent.

13. The method of claim 1 wherein the feed, methylating agent and catalyst are present in a single liquid phase.

14. The method of claim 1 wherein the wherein the feed and catalyst are present in separate liquid phases.

15. The method of claim 1 wherein the catalyst is in the solid phase.

* * * * *